(12) United States Patent
Bongers et al.

(10) Patent No.: US 9,724,050 B2
(45) Date of Patent: Aug. 8, 2017

(54) X-RAY COMPATIBLE INFANT MONITORING AND SUPPORT SYSTEM

(71) Applicant: KONINKLIJKE PHILIPS N.V., Eindhoven (NL)

(72) Inventors: Edwin Gerardus Johannus Maria Bongers, Thorn (NL); Mohammed Meftah, Tilburg (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 56 days.

(21) Appl. No.: 14/356,643

(22) PCT Filed: Nov. 8, 2012

(86) PCT No.: PCT/IB2012/056247
§ 371 (c)(1),
(2) Date: May 7, 2014

(87) PCT Pub. No.: WO2013/076609
PCT Pub. Date: May 30, 2013

(65) Prior Publication Data
US 2014/0307851 A1    Oct. 16, 2014

Related U.S. Application Data

(60) Provisional application No. 61/562,633, filed on Nov. 22, 2011.

(51) Int. Cl.
*A61B 6/00* (2006.01)
*A61B 6/04* (2006.01)
(Continued)

(52) U.S. Cl.
CPC ............ *A61B 6/04* (2013.01); *A61B 5/02055* (2013.01); *A61B 5/1113* (2013.01);
(Continued)

(58) Field of Classification Search
CPC ....... A61B 6/04; A61B 6/0407; A61B 6/0442; A61B 2503/045; A61B 5/0555;
(Continued)

(56) References Cited

U.S. PATENT DOCUMENTS

| 3,888,240 A | 6/1975 | Reinhold et al. |
| 2004/0199072 A1 | 10/2004 | Sprouse et al. |

(Continued)

FOREIGN PATENT DOCUMENTS

| DE | 102009043532 A1 | 9/2010 |
| GB | 1501281 A | 2/1978 |

(Continued)

OTHER PUBLICATIONS

Antonucci et al, "The Infant Incubator in the Neonatal Intensive Care Unit: Unresolved Issues and Future Development", J. Perinat. Med. vol. 37, 2009, pp. 587-598.

(Continued)

*Primary Examiner* — Dani Fox (57) ABSTRACT

Systems and methods for providing infant monitoring and support avoid image degradation, for x-ray imaging, related to sensors used for infant monitoring by separating an infant-supporting body from a sensor-carrying body. The sensor-carrying body, and with it any number of related sensors, is moved out of the way during x-ray imaging.

18 Claims, 5 Drawing Sheets

(51) Int. Cl.
*A61B 5/00* (2006.01)
*A61B 6/08* (2006.01)
*A61B 5/11* (2006.01)
*A61B 5/0205* (2006.01)
*A61G 11/00* (2006.01)

(52) U.S. Cl.
CPC .......... *A61B 5/6887* (2013.01); *A61B 5/6892* (2013.01); *A61B 6/0442* (2013.01); *A61B 6/08* (2013.01); *A61B 6/545* (2013.01); *A61B 6/547* (2013.01); *A61B 6/5252* (2013.01); *A61B 2503/045* (2013.01); *A61B 2560/0443* (2013.01); *A61G 11/00* (2013.01); *A61G 11/002* (2013.01); *A61G 2210/50* (2013.01)

(58) Field of Classification Search
CPC ... A61B 174/2255; A61B 5/721; A61G 11/00; A61G 2210/50
See application file for complete search history.

(56) References Cited

U.S. PATENT DOCUMENTS

2006/0025668 A1 2/2006 Peterson et al.
2007/0036266 A1* 2/2007 Kramp .................. A61B 6/04
378/62
2009/0049611 A1 2/2009 Braunreuther et al.
2009/0129556 A1 5/2009 Ahn
2009/0192384 A1 7/2009 Fontius

FOREIGN PATENT DOCUMENTS

| | | |
|---|---|---|
| JP | 2007185304 A | 7/2007 |
| WO | 03030801 A2 | 4/2003 |
| WO | 2009138976 A2 | 11/2009 |
| WO | 2012143826 A1 | 10/2012 |

OTHER PUBLICATIONS

Arroe, "The Risk of X-Ray Examinations of the Lungs in Neonates", Acta Padiatr Scand, vol. 80, 1991, pp. 489-493.

Whit et al, "Short- and Long-Term Impact of Neonatal Pain and Stress: More Than an Ouchie" Neo Reviews, vol. 6, No. 2, 2005, p. E69-E75.

Mutch et al, "Imaging the Neonate in the Incubator: An Investigation of the Technical, Radiological and Nursing Issues", The British Journal of Radiology, vol. 80, 2007, pp. 902-910.

* cited by examiner

X-RAY COMPATIBLE INFANT MONITORING AND SUPPORT SYSTEM

CROSS-REFERENCE TO PRIOR APPLICATIONS

This application is the U.S. National Phase application under 35 U.S.C. §371 of International Application No. PCT/IB2012/056247, filed on Nov. 8, 2012, which claims the benefit of U.S. Provisional Patent Application No. 61/562,633, filed on Nov. 22, 2011. These applications are hereby incorporated by reference herein.

The present disclosure pertains to systems and methods for providing infant monitoring and support that is compatible with x-ray imaging, and, in particular, the combination of a separately movable infant-supporting body and a sensor-carrying body.

It is well known to monitor the status of infants, e.g. neonates, in intensive care environments. It is well-known that monitoring and/or measuring physiological parameters of an infant, or other clinically relevant information, may commonly be accomplished by using sensors. It is well-known that x-ray imaging may provide important clinical information regarding the status of an infant. It is well-known that many sensors are visible in x-ray images and contribute to image degradation in such images.

Accordingly, it is an object of one or more embodiments of the present invention to provide an x-ray-compatible infant monitoring and support system. The system comprises a sensor-carrying body configured to carry one or more sensors; one or more sensors carried by the sensor-carrying body, wherein the one or more sensors are configured to generate one or more output signals conveying information related to one or more physiological parameters of an infant; and an infant-supporting body configured to support an infant on a top-surface of the infant-supporting body. The infant-supporting body is configured to be disposed on top of the sensor-carrying body, such that the one or more sensors carried by the sensor-carrying body generate one or more output signals conveying information related to one or more physiological parameters of the supported infant. The sensor-carrying body and infant-supporting body comprise different structures such that the sensor-carrying body and the infant-supporting body can be separated to facilitate capture of an x-ray image of the supported infant that is uncorrupted by image degradation related to the one or more sensors.

It is yet another aspect of one or more embodiments of the present invention to provide a method of providing x-ray-compatible infant monitoring and support. The method comprises supporting an infant on a top-surface of an infant-supporting body, wherein the infant-supporting body is being disposed on top of a sensor-carrying body; generating, by one or more sensors being carried by the sensor-carrying body, one or more output signals conveying information related to one or more physiological parameters of the supported infant; and separating the sensor-carrying body from the infant-supporting body to facilitate capture of an x-ray image of the supported infant such that the captured x-ray image is uncorrupted by image degradation related to the one or more sensors.

It is yet another aspect of one or more embodiments to provide a system configured to provide x-ray-compatible infant monitoring and support. The system comprises means for supporting an infant, wherein the means for supporting the infant is being disposed on top of means for carrying one or more sensors; means for carrying one or more sensors configured to generate one or more output signals conveying information related to one or more physiological parameters of the supported infant; and means for separating the means for carrying one or more sensors from the means for supporting the infant to facilitate capture of an x-ray image of the supported infant such that the captured x-ray image is uncorrupted by image degradation related to the one or more sensors.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
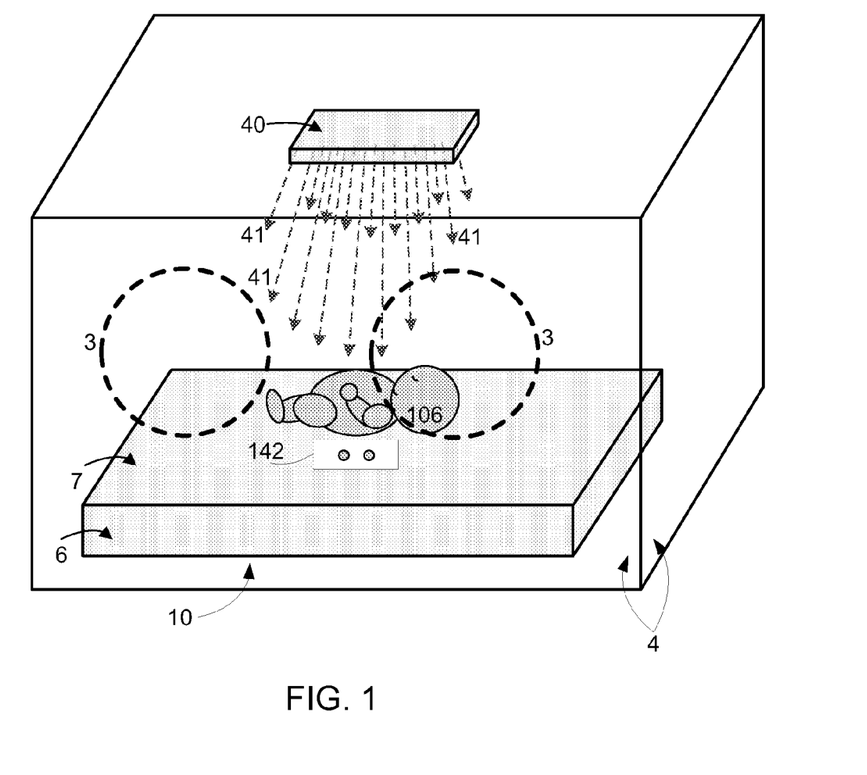
FIG. 1 illustrates a system for infant monitoring and support.

FIG. 1 illustrates a system 10 for infant monitoring and support. System 10 may include one or more of an infant-supporting body 6, one or more sensors 142, an incubator 4, an x-ray tube 40, and/or other components. Infant-supporting body 6 may include a top-surface 7 and be configured to support on infant 106 on top-surface 7. Top-surface 7 may engage infant 106 during use of system 10. In other words, infant 106 may be placed on top-surface 7 during use of system 10. In some embodiments, system 10 may be integrated, embedded, and/or combined with one or more of an incubator 4, an x-ray tube 40, and/or other components. Incubator 4 may include one or more access windows 3. X-ray tube 40 may emit electromagnetic radiation 41, which may be used for imaging purposes.

The status of infant 106 may be monitored, e.g. through one or more sensors 142, while infant 106 is being placed on and/or supported by infant-supporting body 6. In general, it may be preferable not to move, mechanically jostle, relocate, pick up, lift from infant-supporting body 6, or otherwise disturb infant 106 (collectively referred to hereinafter as "disturb") unless necessary. An x-ray image captured of infant 106, e.g. by x-ray tube 40 arranged above infant 106, may be corrupted by image degradation related to one or more sensors 142 disposed near infant 106. In other words, one or more sensors 142 and/or associated wiring or electronics may be captured and/or visible in the x-ray image. Such image degradation may affect the quality of that image and/or the amount of useful information within that image.

Figure 2A:
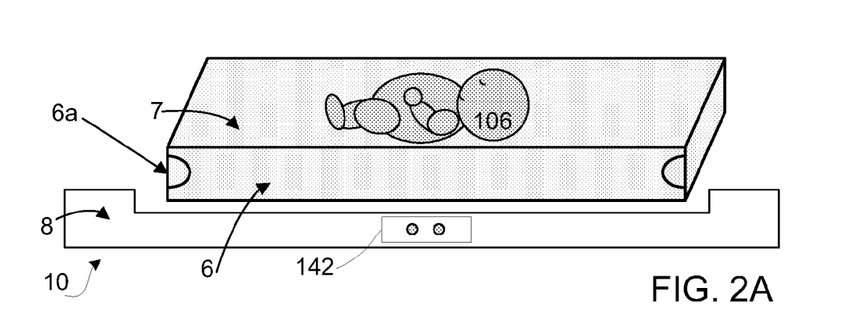
FIGS. 2A-C illustrate x-ray-compatible monitoring and support systems including an infant-supporting body and a sensor-carrying body, in accordance with one or more embodiments.

An x-ray-compatible system 10 for monitoring and supporting infant 106 may include separate and movable bodies corresponding to the monitoring and supporting functions. By way of illustration, FIG. 2A illustrates an x-ray-compatible monitoring and support system 10 including infant-supporting body 6 and a sensor-carrying body 8, in accordance with one or more embodiment. As depicted in FIG. 2A, infant 106 is placed on top-surface 7 of infant-supporting body 6. One or more sensors 142 are carried by sensor-carrying body 8 (depicted in side view in FIG. 2A), which is separate and movable (i.e. moved out of the imaging area during x-ray imaging) from infant-supporting body 6. Infant-supporting body 6 may be configured to be disposed on top of sensor-carrying body 8, such that the one or more sensors 142 carried by sensor-carrying body 8 generate one or more output signals conveying information related to one or more physiological parameters of infant 106 as the infant is being supported on infant-supporting body 6. In some embodiments, infant-supporting body 6 may include one or more handles 6a, such that a user 108 (not shown in FIG. 2A), such as, e.g., a nurse, a doctor, a caregiver, a healthcare professional, etc., may lift infant-supporting body 6, together with infant 106, and thus separate infant-supporting body 6 from sensor-carrying body 8. By physically and/or manually separating sensor-carrying body 8 from infant-supporting body 6, system 10 facilitates capture of an x-ray image of infant 106 such that the captured x-ray image may be uncorrupted by image degradation related to the one or more sensors 142.

Figure 2B:
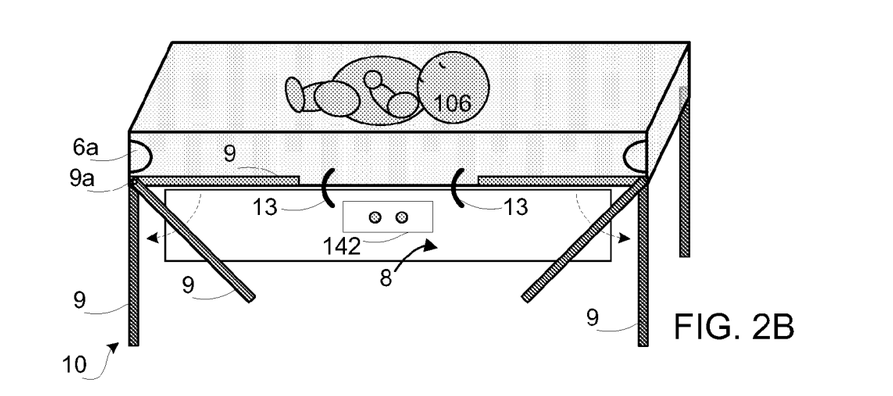

In some embodiments, it may be desirable that a single user 108 may operate system 10 to facilitate x-ray imaging of infant 106. By way of illustration, FIG. 2B illustrates an x-ray-compatible monitoring and support system 10 including not only infant-supporting body 6 and sensor-carrying body 8, but also one or more releasable support bodies 9. The one or more releasable support bodies 9 may be releasably coupled to infant-supporting body 6, e.g. though one or more mechanical connectors 9a, such as a joint, hinge, pin, and/or other coupling. The one or more releasable support bodies may be released automatically, manually, and/or through a combination of actions initiated and/or caused by user 108 (not shown in FIG. 2B). Once the one or more releasable support bodies 9 are released and/or deployed, user 108 may use one or more mechanical separators 13 to physically and/or mechanically separate sensor-carrying body 8 from infant-supporting body 6. In some embodiments, mechanical separator 13 operates by slidable engagement, such as, e.g., exemplified by a drawer sliding out of a desk. In some embodiments, mechanical separator 13 operates by a pivotable coupling between sensor-carrying body 8 and infant-supporting body 6, such as, e.g., exemplified by opening a laptop. In some embodiments, mechanical separator 13 operates by a releasable coupling such as, e.g., exemplified by a (reusable) fastener such as Velcro®. Note that none of these examples are intended to be limiting in scope, but are merely used to illustrate various features of one or more embodiments.

Figure 2C:
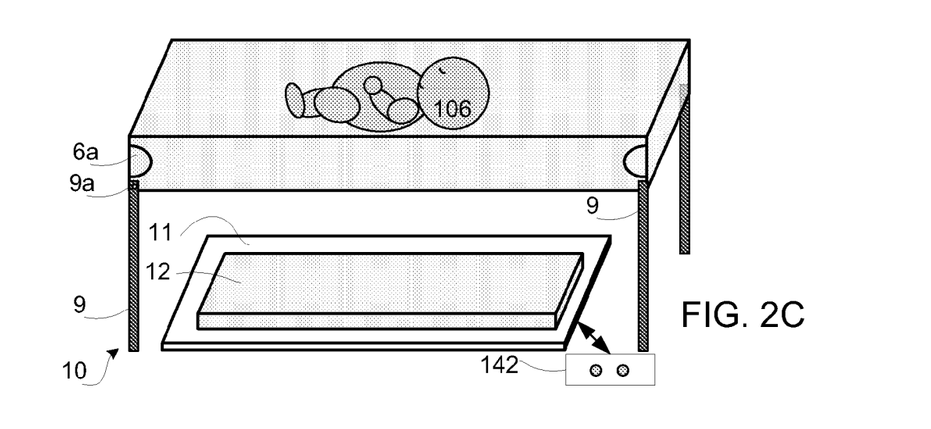
Figure 3:
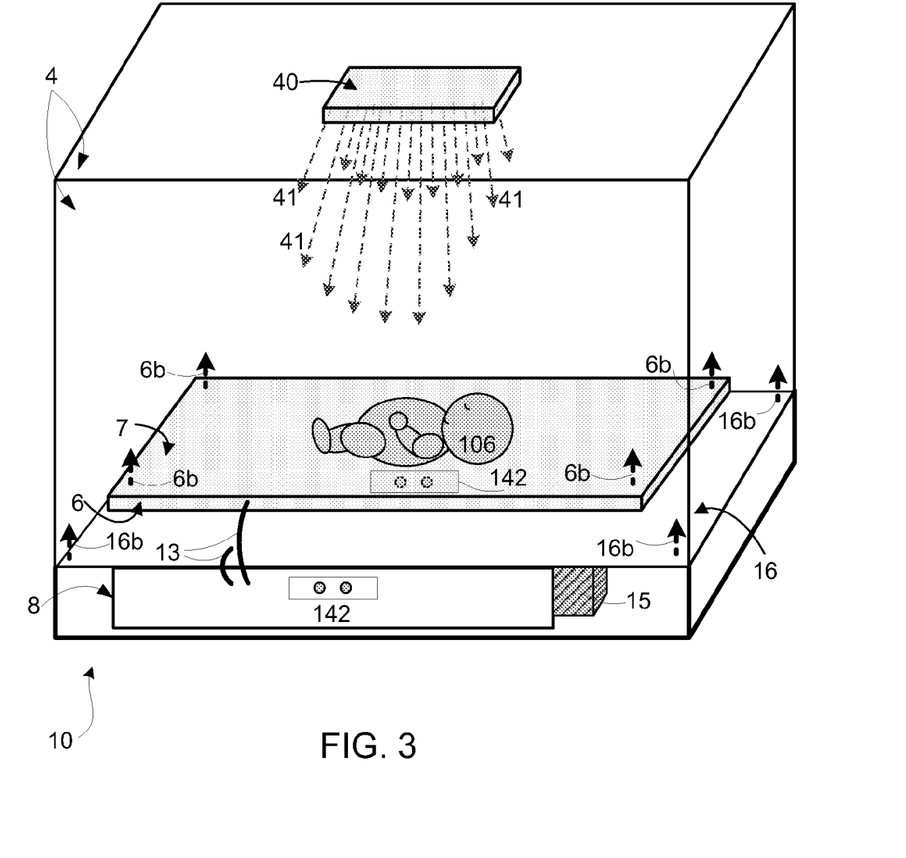
FIG. 3 illustrates a system for x-ray-compatible infant monitoring, in accordance with one or more embodiments.

Once user 108 has separated (and/or caused to separate) sensor-carrying body 8 from infant-supporting body 6, a tray 11 (see FIG. 2C) may be placed, including and/or carrying an x-ray detector 12 that is suitable for x-ray imaging, under and/or below infant 106, or in another position suitable for x-ray imaging. By way of illustration, FIG. 2C illustrates an x-ray-compatible monitoring and support system 10 including one or more released and/or deployed releasable support bodies 9, tray 11, x-ray image detector 12, and/or other components. Alternatively, and/or simultaneously, one or more releasable support bodies may otherwise be mechanically coupled to infant-supporting body 6. For example, system 10 may include a substantially rigid frame that connects to both infant-supporting body 6 and one or more releasable support bodies 9. System 10 may include one or more sensors 142 configured to generate output signals conveying information pertaining to a position of tray 11 and/or x-ray image detector 12. One or more of these sensors may be referred to, in the context of FIG. 2C, as tray position sensors 142. The conveyed information may be used to determine whether infant 106 is properly aligned with tray 11 and/or x-ray image detector 12 for the purpose of x-ray imaging. After the x-ray image has been captured, sensor-carrying body 8 may be returned to its original position, such that the one or more sensors 142 carried by sensor-carrying body 8 may continue to be used for monitoring the status of infant while infant 106 is being supported on infant-supporting body 6.

Sensor(s) 142 of system 10 in FIGS. 2A-C and/or other figures may be configured to generate output signals conveying information related to the age, position, posture, size, weight, and/or status of infant 106, physiological, environmental, and/or infant-specific (medical) parameters related to infant 106, and/or other information. System 10 may use any of the generated output signals to monitor infant 106. In some embodiments, the conveyed information may be related to parameters associated with the state and/or condition of infant 106, the breathing of infant 106, the gas breathed by infant 106, the heart rate of infant 106, the respiratory rate of infant 106, vital signs of infant 106, including one or more temperatures, oxygen saturation of arterial blood ($SpO_2$), whether peripheral or central, and/or other parameters. Individual sensors or subsets of sensors from sensors 142 may be designated by specific functions, such as, e.g., an infant position sensor, a tray position sensor, and/or other sensors.

As a non-limiting example, one or more sensors 142 may generate one or more output signals conveying information related to a (three-dimensional) position of infant 106 on top-surface 7, e.g. through stereoscopy. Sensors 142 may include one or more of a temperature sensor, a pressure/weight sensor, a light sensor, one or more still-image cameras, one or more video cameras, and/or other sensors.

The illustration of sensor 142 including two members in FIGS. 2A-C is not intended to be limiting. System 10 may include one or more sensors. Resulting signals or information from one or more sensors 142 may be transmitted to processor 110, user interface 120, electronic storage 130, and/or other components of system 10. This transmission can be wired and/or wireless. Monitoring of infant 106 may be based on one or more sensors 142 and/or any of the related parameters described herein. Monitoring and/or measuring may be used as a contact-less, non-invasive means to obtain information. "Contact-less" refers to either refraining from the use of adhesives (e.g. on the skin of infant 106) and/or refraining from direct skin contact in the context of this disclosure. Note that any sensor described herein is contemplated to be contact-less.

In some embodiments, the function of system 10 needs to be accomplished within an incubator environment, such that the micro-climate within the incubator (including one or more of an internal temperature, humidity, and/or other characteristics of a micro-climate within an incubator), e.g. incubator 4, is left substantially undisturbed during x-ray imaging. By way of illustration, FIG. 3 illustrates a system 10 for infant monitoring, embedded within incubator 4. As depicted in FIG. 3, system 10 may include a lifting tray 16, upon which infant-supporting body 6 may be disposed. Lifting tray may be configured to function as a micro-climate barrier, such that user access to components of system 10 below lifting tray 16 may not substantially affect the micro-climate in the cavity of incubator 4 in which infant 106 is placed. System 10 may include a lifting/lowering mechanism 15, which may be configured to, upon activation, separate lifting tray 16, infant-supporting body 6, infant 106, and/or any combination thereof from sensor-carrying body 8, e.g. by lifting at least infant 106. Alternatively, and/or simultaneously, lifting/lowering mechanism 15 may be configured to, upon activation, lower sensor-carrying body 8 or otherwise separate sensor-carrying body 8 from infant-supporting body 6, infant 106, and/or any combination thereof. One possible motion and/or direction of lifting is depicted by dotted lifting arrows 16b and dotted lifting arrows 6b in FIG. 3. The depicted motion and/or direction is meant to be exemplary, and is not intended to be limiting in any way. In the example depicted in FIG. 3, once at least infant 106 is lifted and/or raised up, sensor-carrying body 8 may be separated from infant-supporting body 6, e.g. manually. At such a time, tray 11 (not shown in FIG. 3) and/or x-ray detector 12 (not shown in FIG. 3) may be placed under infant-supporting body (e.g. in the original location/place of sensor-carrying body 8). X-ray tube 40 may emit electromagnetic radiation 41, which may be used for imaging purposes. Thus, system 10 as depicted in FIG. 3 facilitates capture of an x-ray image of supported infant 106 that is uncorrupted by image degradation related to one or more sensors 142. As depicted in FIG. 3, operation of system 10 may be accomplished such that infant 106 and/or a micro-climate around infant 106 are substantially left undisturbed during x-ray imaging.

Figure 4:
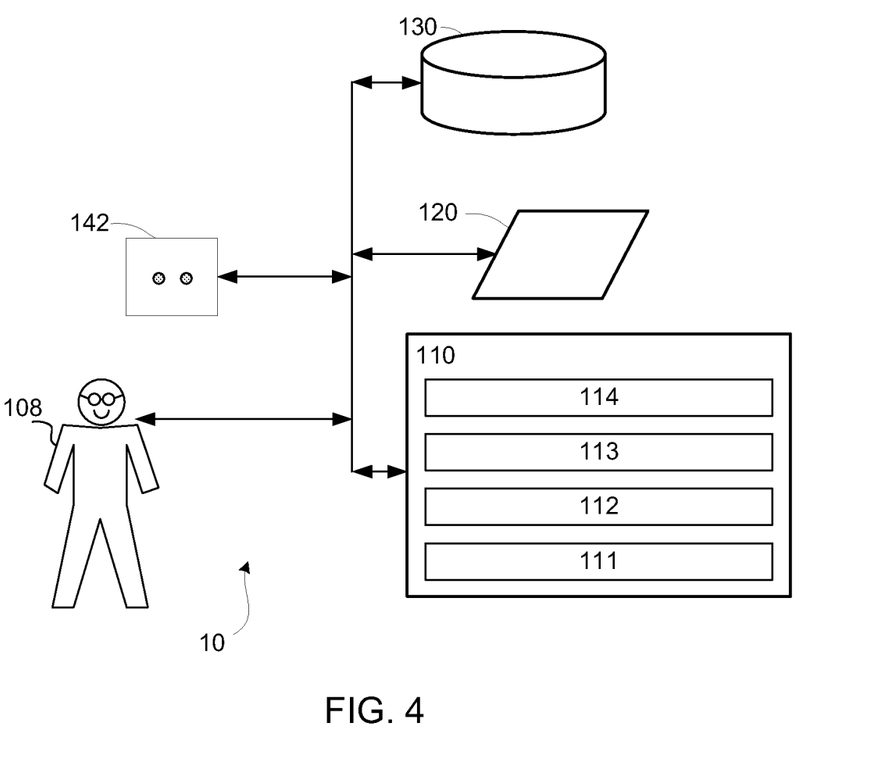
FIG. 4 schematically illustrates a system for infant monitoring, in accordance with one or more embodiments.

FIG. 4 schematically illustrates an x-ray-compatible infant monitoring and support system 10 in accordance with one or more embodiments. System 10 may include, in addition to any previously mentioned components in this description, one or more of a processor 110, a user-interface 120, electronic storage 130, one or more executable computer program modules including, but not limited to, an infant position module 111, a tray position module 112, an alignment module 113, a notification module 114, and/or other components.

User interface 120 of system 10 in FIG. 4 may be configured to provide an interface between system 10 and user 108 through which the user can provide information to and/or receive information from system 10. This enables data, results, and/or instructions and any other communicable items, collectively referred to as "information," to be communicated between the user and system 10. An example of information that may be conveyed to user 108 is alignment information regarding infant 106, tray 11, and/or x-ray detector 12. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 by user interface 120 in the form of auditory signals, visual signals, tactile signals, and/or other sensory signals, or any combination thereof.

By way of non-limiting example, user interface 120 may include a radiation source capable of emitting light. The radiation source may include, for example, one or more of at least one LED, at least one light bulb, a display screen, and/or other sources. User interface 120 may control the radiation source to emit light in a manner that conveys to user 108 information related to the aforementioned alignment.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 10 from removable storage (e.g., a smart card, a flash drive, a removable disk, etc.) that enables the user(s) to customize the implementation of system 10. Other exemplary input devices and techniques adapted for use with system 10 as user interface 120 include, but are not limited to, an RS-232 port, RF link, an IR link, modem (telephone, cable, Ethernet, internet or other). In short, any technique for communicating information with system 10 is contemplated as user interface 120.

Electronic storage 130 of system 10 in FIG. 4 comprises electronic storage media that electronically stores information. The electronic storage media of electronic storage 130 may include one or both of system storage that is provided integrally (i.e., substantially non-removable) with system 10 and/or removable storage that is removably connectable to system 10 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 10 to function properly. For example, electronic storage 130 may record or store information related to the captured x-ray images, and/or other information. Electronic storage 130 may be a separate component within system 10, or electronic storage 130 may be provided integrally with one or more other components of system 10 (e.g., processor 110).

Processor 110 of system 10 in FIG. 4 is configured to provide information processing capabilities in system 10. As such, processor 110 includes one or more of a digital processor, an analog processor, a digital circuit designed to process information, an analog circuit designed to process information, a state machine, and/or other mechanisms for electronically processing information. Although processor 110 is shown in FIG. 4 as a single entity, this is for illustrative purposes only. In some implementations, processor 110 includes a plurality of processing units.

As is shown in FIG. 4, processor 110 is configured to execute one or more computer program modules. The one or more computer program modules include one or more of a parameter determination module, an infant position module 111, a tray position module 112, an alignment module 113, a notification module 114, and/or other modules. Processor 110 may be configured to execute modules 111, 112, 113 and/or 114 by software; hardware; firmware; some combination of software, hardware, and/or firmware; and/or other mechanisms for configuring processing capabilities on processor 110.

It should be appreciated that although modules 111, 112, 113, and 114 are illustrated in FIG. 4 as being co-located within a single processing unit, in implementations in which processor 110 includes multiple processing units, one or more of modules 111, 112, 113 and/or 114 may be located remotely from the other modules. The description of the functionality provided by the different modules 111, 112, 113 and/or 114 described below is for illustrative purposes, and is not intended to be limiting, as any of modules 111, 112, 113 and/or 114 may provide more or less functionality than is described. For example, one or more of modules 111, 112, 113 and/or 114 may be eliminated, and some or all of its functionality may be provided by other ones of modules 111, 112, 113 and/or 114. Note that processor 110 may be configured to execute one or more additional modules that may perform some or all of the functionality attributed below to one of modules 111, 112, 113 and/or 114.

A parameter determination module of system 10 (not shown) may be configured to determine one or more status parameters, medical parameters, and/or other parameters from output signals generated by one or more sensors 142. Parameters may be related to an infant's age, size, volume, weight, and/or other physiological, environmental, and/or infant-specific parameters. One or more status parameters may be related to the presence, posture, and/or position of infant 106. One or more medical parameters may be related to monitored vital signs of infant 106, and/or other medical parameters of infant 106. Other parameters may be related to the environment near system 10 or within incubator 4, such as, e.g., air temperature. Some or all of this functionality may be incorporated or integrated into other computer program modules of processor 110.

Infant position module 111 of system 10 in FIG. 4 is configured to determine one or more of the presence, (three-dimensional) position, posture, and/or orientation of infant 106 (and/or anatomical parts including but not limited to the eyes, one or more legs, one or more arms, head, forehead, and/or other anatomical parts of infant 106). The determination by infant position module 111 may be based on information from one or more sensors 142, such as information from, e.g., one or more infant position sensors, and/or through stereoscopy using multiple cameras. In some embodiments, infant position module 111 may be configured to determine in which area (and/or in which posture and/or orientation) on top-surface 7 of infant-supporting body 6 exposed skin of infant 106, e.g. the head or feet of the infant, is currently located.

Tray position module 112 of system 10 in FIG. 4 is configured to determine the presence, (three-dimensional) position, and/or orientation of tray 11 (and/or x-ray detector 12). The determination by tray position module 112 may be based on information from one or more sensors 142, such as information from, e.g., one or more tray position sensors, and/or through stereoscopy using multiple cameras.

Alignment module 113 of system 10 in FIG. 4 is configured to determine whether infant 106, while being supported by infant-supporting body 6, is aligned with tray 11 and/or x-ray detector 12. This determination may be based on one or more of a determination of the position of infant 106, a determination of a position of tray 11, a determination of the position of x-ray detector 12, information relation to a position of x-ray tube 40, and/or other information.

Notification module 114 of system 10 in FIG. 4 may be configured to present an alignment notification based on a determination by alignment module 113 to user 108. Notification module 114 may operate in conjunction with user interface 120 to present a notification to user 108.

Figure 5:
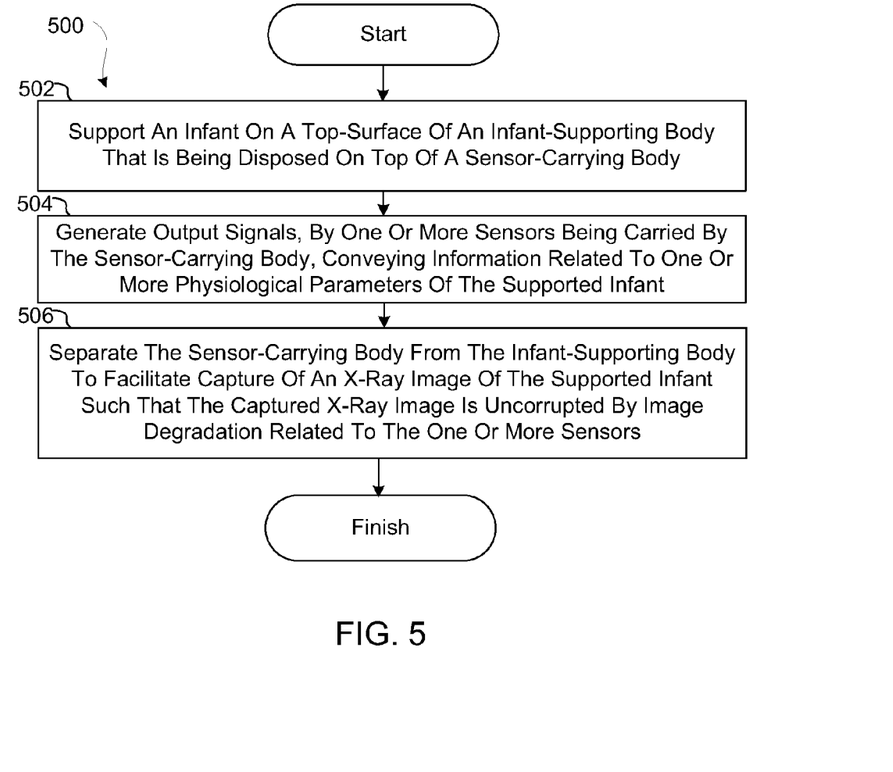
FIG. 5 illustrates a method for providing x-ray-compatible infant monitoring and support, in accordance with one or more embodiments.

FIG. 5 illustrates a method 500 for providing x-ray compatible infant monitoring and support. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting.

In some embodiments, method 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

At an operation 502, an infant is supported on a top-surface of an infant-supporting body. In one embodiment, operation 502 is performed by an infant-supporting body similar to or substantially the same as infant-supporting body 6 (shown in FIG. 2A and described above).

At an operation 504, one or more output signals are generated that convey information related to one or more physiological parameters of the supported infant. In one embodiment, operation 504 is performed by one or more sensors similar to or substantially the same as the one or more sensors 142 that are carried by sensor-carrying body 8 (shown in FIG. 2A and described above).

At an operation 506, the sensor-carrying body is separated from the infant-carrying body to facilitate capture of an x-ray image such that the captured x-ray image is uncorrupted by image degradation related to the one or more sensors. In one embodiment, operation 506 is accomplished by using one or more mechanical separators similar to or substantially the same as mechanical separator 13 (shown in FIG. 2B and described above).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. An x-ray-compatible infant monitoring and support system comprising:
    a sensor-carrying body configured to carry one or more sensors;
    one or more sensors carried by the sensor-carrying body, wherein the one or more sensors are configured to generate one or more output signals conveying information related to one or more physiological parameters of an infant, the one or more physiological parameters including one or more of a heart rate, a respiration rate, a temperature, or an oxygen saturation level of the infant;
    an infant-supporting body configured to support an infant on a top-surface of the infant-supporting body;
    a lifting tray, wherein the infant-supporting body is configured to be disposed on the lifting tray, the lifting tray including a lifting/lowering mechanism, the lifting/lowering mechanism being configured to lower the sensor-carrying body to separate the sensor-carrying body from the infant-supporting body,
    wherein the sensor-carrying body is moveable relative to the infant-supporting body, while remaining attached to the x-ray-compatible infant monitoring and support system, to facilitate capture of an x-ray image of the supported infant that is uncorrupted by image degradation related to the one or more sensors.

2. The system claim 1, further comprising an x-ray tray including an x-ray detector suitable for x-ray imaging, the x-ray tray configured to replace the sensor-carrying body under the infant-supporting body.

3. The system of claim 1, wherein the lifting/lowering mechanism is configured to lift the infant supporting body to separate the sensor-carrying body from the infant-supporting body.

4. The system of claim 1, wherein the lifting/lowering mechanism is configured to lift the lifting tray to separate the sensor-carrying body from the infant-supporting body.

5. The system of claim 1, further comprising:
    an x-ray tray including an x-ray detector, wherein the x-ray detector is suitable for x-ray imaging;
    one or more infant position sensors configured to generate one or more output signals conveying three dimensional position information of the supported infant;
    one or more tray position sensors configured to generate one or more output signals conveying position information of the tray; and
    one or more processors configured to execute computer program modules, the computer program modules comprising:
    an infant position module configured to determine a three dimensional position of the supported infant based on the position information of the infant;
    an x-ray position module configured to determine a position of the tray based on the position information of the tray;
    an alignment module configured to determine whether the supported infant is aligned with the x-ray tray for imaging purposes, wherein a determination by the alignment module is based on a determination of the position of the infant by the infant position module and a determination of the position of the x-ray tray by the tray position module; and
    a notification module configured to present a user with an alignment notification based on the determination by the alignment module.

6. A method of providing x-ray-compatible infant monitoring and support with an x-ray-compatible infant monitoring and support system, the method comprising:
    supporting an infant on a top-surface of an infant-supporting body, the infant supporting body being disposed on a lifting tray, the lifting tray including a lifting/lowering mechanism, wherein the infant-supporting body is being disposed on top of a sensor-carrying body;
    generating, by one or more sensors being carried by the sensor-carrying body, one or more output signals conveying information related to one or more physiological parameters of the supported infant, the one or more physiological parameters including one or more vital signs of the supported infant; and
    separating the sensor-carrying body from the infant-supporting body to facilitate capture of an x-ray image of the supported infant such that the captured x-ray image is uncorrupted by image degradation related to the one or more sensors, wherein separating the sensor-carrying body from the infant-supporting body is accomplished by activating the lifting/lowering mechanism to lower the sensor-carrying body to separate the sensor-carrying body from the infant-supporting body, while the sensor-carrying body remains attached to the x-ray-compatible infant monitoring and support system.

7. The method of claim 6, wherein separating the sensor-carrying body from the infant-supporting body is accomplished by activating the lifting/lowering mechanism to lift the infant support body, the method further comprising replacing the sensor-carrying body under the infant-supporting body with an x-ray tray that includes an x-ray detector suitable for x-ray imaging.

8. The method of claim 6, wherein separating the sensor-carrying body from the infant-supporting body is accomplished by activating the lifting/lowering mechanism to lift the lifting tray.

9. The method of claim 6, wherein separating the sensor-carrying body from the infant-supporting body is accomplished by a slidable engagement therebetween.

10. The method of claim 6, further comprising:
    providing an x-ray detector that is suitable for x-ray imaging;
    generating, by one or more infant position sensors, one or more output signals conveying three dimensional position information of the supported infant;
    determining a three dimensional position of the supported infant based on the position information of the supported infant;
    generating, by one or more tray position sensors, one or more output signals conveying position information of the x-ray detector;
    determining a position of the x-ray detector based on the position information of the x-ray detector;

determining whether the supported infant is aligned with the x-ray detector for imaging purposes, wherein the determination is based on the determined position of the supported infant and the determined position of the x-ray detector; and presenting a user with an alignment notification based on the determination whether the supported infant is aligned with the x-ray detector for imaging purposes.

11. A system configured to provide x-ray-compatible infant monitoring and support, the system comprising:

means for supporting an infant, wherein the means for supporting the infant is being disposed on a lifting means, the lifting means including a lifting/lowering mechanism, wherein the means for supporting the infant is disposed on top of means for carrying one or more sensors;

means for carrying one or more sensors configured to generate one or more output signals conveying information related to one or more physiological parameters of the supported infant, the one or more physiological parameters including one or more vital signs of the supported infant; wherein the means for carrying one or more sensors is moveable relative to the means for supporting an infant, while remaining attached to the system configured to provide x-ray-compatible infant monitoring and support; and means for separating the means for carrying one or more sensors from the means for supporting the infant to facilitate capture of an x-ray image of the supported infant such that the captured x-ray image is uncorrupted by image degradation related to the one or more sensors, wherein separating the means for carrying from the means for supporting is accomplished by activating the lifting/lowering mechanism to lower the means for carrying to separate the means for carrying from the means for supporting.

12. The system of claim 11, further comprising means for x-ray detection suitable for x-ray imaging, wherein the means for separating operates by activating the lifting/lowering mechanism to lift the means for supporting the infant and the means for supporting the infant and the means for x-ray detection replaces the means for carrying one or more sensors under the means for supporting the infant.

13. The system of claim 11, wherein the means for separating operates by activating the lifting/lowering mechanism to lift the lifting means.

14. The system of claim 11, wherein the means for separating operates by slidable engagement between the means for carrying one or more sensors and the means for supporting the infant.

15. The system of claim 11, further comprising:

means for detecting x-rays that is suitable for x-ray imaging, means for generating one or more output signals conveying three dimensional position information of the supported infant;

means for determining a three dimensional position of the supported infant based on the position information of the supported infant;

means for generating one or more output signals conveying position information of the means for detecting x-rays;

means for determining a position of the means for detecting x-rays based on the position information of the means for detecting x-rays;

means for determining whether the supported infant is aligned, for imaging purposes, with the means for detecting x-rays, wherein the determination is based on the determined position of the supported infant and the determined position of the means for detecting x-rays; and means for presenting a user with an alignment notification based on the determination whether the supported infant is aligned with the means for detecting x-rays.

16. The system of claim 3, further comprising an incubator configured to form an incubator environment having a micro-climate around the infant, wherein the lifting tray forms a microclimate barrier, and wherein the lifting tray engages the incubator such that lowering the sensor-carrying body or lifting the infant-supporting body to separate the sensor-carrying body from the infant-supporting body does not substantially affect the micro-climate of the incubator environment.

17. The method of claim 7 further comprising forming an incubator environment having a micro-climate around the infant with an incubator, wherein the lifting tray forms a microclimate barrier, and wherein the lifting tray engages the incubator such that lowering the sensor-carrying body or lifting the infant-supporting body to separate the sensor-carrying body from the infant-supporting body does not substantially affect the micro-climate of the incubator environment.

18. The system of claim 12 further comprising an incubator configured to form an incubator environment having a micro-climate around the infant, wherein the lifting means forms a microclimate barrier, and wherein the lifting means engages the incubator such that lowering the means for carrying the one or more sensors or lifting the means for supporting the infant to separate the means for carrying the one or more sensors from the means for supporting the infant does not substantially affect the micro-climate of the incubator environment.

* * * * *